US00PP16818P2

(12) United States Plant Patent
Olbricht

(10) Patent No.: US PP16,818 P2
(45) Date of Patent: Jul. 18, 2006

(54) **VARIETY OF *ANGELONIA* PLANT NAMED 'ANPINK'**

(50) Latin Name: ***Angelonia* hybrid**
Varietal Denomination: Anpink

(75) Inventor: Klaus Olbricht, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 126 days.

(21) Appl. No.: 11/059,197

(22) Filed: Feb. 16, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—The Webb Law Firm

(57) ABSTRACT

A new and distinct flowering *Angelonia* plant with dark leaves and large pink flowers.

2 Drawing Sheets

Botanical classification: *Angelonia* hybrid.
Varietal denomination: 'Anpink'.

BACKGROUND OF THE INVENTION

The present invention comprises a new and distinct cultivar of *Angelonia* hybrid known by the varietal name 'Anpink'. The new variety was discovered in a selected breeding program in Dresden, Germany. The new variety is the result of a cross combination breeding between a bulk of unnamed and unpatented selections from a collection of proprietary breeding plants (Group OK-113). The purpose of the breeding program was to find a new variety with large pink flowers. The new variety was first asexually reproduced in 2002 by cuttings in Dresden, Germany. The new variety has been trial and field tested in Dresden and has been found to retain its distinctive characteristics and remain true to type through successive propagations. Characteristics distinguishable from other varieties include:

Upright plant habit

Large flowers

More intense pink flower color

Dark green leaves

DESCRIPTION OF THE DRAWINGS

The accompanying photographic drawings illustrate the new variety, with the color being as nearly true as is possible with color illustrations of this type.

Figure 1:
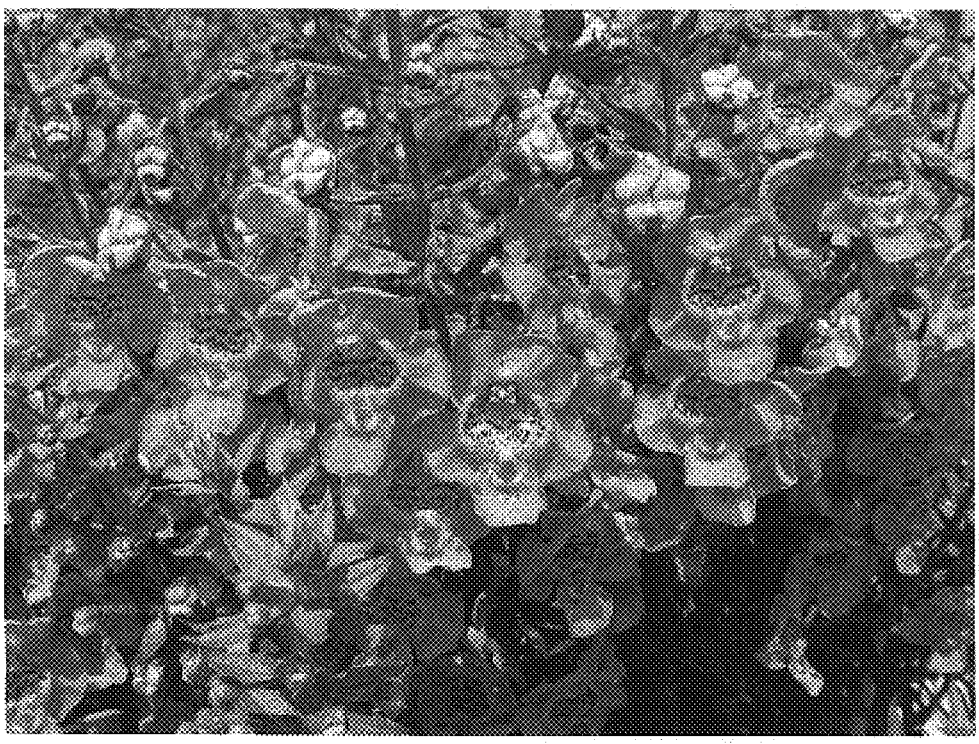
FIG. 1 is a close-up view of the flowers of the new variety.
Figure 2:
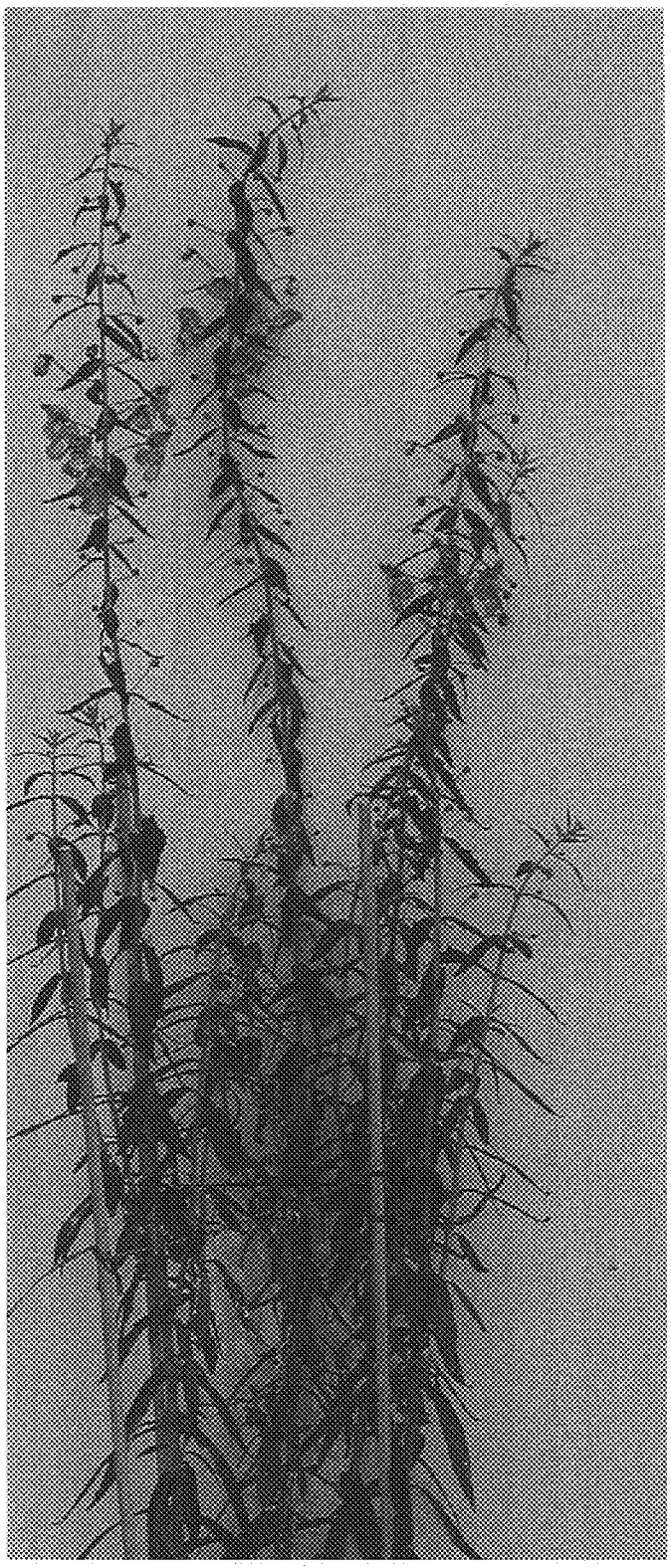
FIG. 2 is a view of entire plants of the new variety.

DESCRIPTION OF THE PLANT the following detailed description sets forth the characteristics of the new cultivar. The data that defines these characteristics were collected by asexual reproductions carried out in a warm greenhouse in Dresden, Germany. The color readings were taken on a plant indoors under natural light. The new variety was six months old when described. Color references are primarily to The R.H.S. Colour Chart of The Royal Horticultural Society of London.

PLANT

Form: Upright.
Height: 75 cm from soil to top of foliage and racemose.
Diameter: 25 cm.
Growth: Erect, with moderate branching and vigor.
Time to initiate roots: About 10 days at 22° C.
Time to develop roots: About 30 days at 22° C.
Container size: 19 cm.
Main stem:
- *Form.*—Upright.
- *Color.*—144A.
- *Texture.*—Hairy, very sticky.
- *Length.*—Approximately 60 cm.
- *Diameter.*—4–5 mm.
- *Internode length.*—1–3 cm.

Foliage:
- *Arrangement (e.g., alternate single).*—Opposite, decussate.
- *Number of leaves per branch.*—Many.
- *Size of leaf.*—Length: 3–9 cm. Width: 1 cm.
- *Shape of leaf (generally).*—Lanceolate.
- *Shape of apex.*—Pointed.
- *Shape of base.*—Pointed.
- *Texture.*—Smooth.
- *Aspect.*—Horizontal to slightly hanging.
- *Margin type.*—Finely serrated.
- *Color.*—Young leaves: Upper surface: 137A. Lower surface: 137C. Mature leaves: Upper surface: 137A. Lower surface: 137C.
- *Petiole.*—Not present, leaves are directly connected to the stem.
- *Veins.*—Venation type: Pinnate. Color: Upper surface: 137A. Lower surface: 144C.

FLOWER

Natural flowering season at specified location(s): In Middle Europe, outdoors from middle of May until frost.
Flower type and habit: 1 flower per leaf axil.
Number of flowers per plant: Plenty.
Bud (described when the tips of the petals are visible):
- *Shape.*—Globose.
- *Diameter.*—5 mm.
- *Length.*—5 mm.
- *Color.*—139B.

Flower:

*Shape.*—5 petals, basal fused together ending in a pharynx, the petals are slightly undulated.

*Diameter.*—24 mm.

*Length.*—28 mm.

*Depth.*—0.5 cm.

*Petal length.*—7 mm.

*Petal width.*—12 mm.

*Petal apex shape.*—Round.

*Petal margin.*—Smooth, undulating.

*Texture.*—Smooth, velvety.

*Color.*—When opening: Upper surface: Upper petals 67D, the pharynx has a white, 155A, eye with dark purple, 187A, spots. Lower surface: 73B. Fully opened: Upper surface: Upper petals 67D, the pharynx has a white, 155A, eye with dark purple, 187A, spots. Lower surface: 73B.

Sepal:

*Number.*—5.

*Length.*—5 mm.

*Width.*—3 mm.

*Shape.*—Between lanceolate and elliptic.

*Apex.*—Pointed.

*Base.*—Fused.

*Margin.*—Entire.

*Color.*—139B (Both surfaces).

Peduncle:

*Length.*—2 cm.

*Diameter.*—1 mm.

*Color.*—144A.

*Orientation.*—Angled 45° upright.

*Strength.*—Elastic.

Pedicel: Absent.

Disease resistance: None observed at this time.

Fragrance: Absent.

Weather tolerance: Susceptible to cold temperatures.

*Lastingness of the bloom.*—About 20 days on the plant.

*Seed production and description.*—Light brown, very small (approximately 0.13 g/100 seeds).

*Fruit production and description.*—Rarely observed. When present, they are green capsules with approximately 50 seeds per capsula. When seeds are brown and dry clasping they measure in diameter approximately 0.5 cm.

REPRODUCTIVE ORGANS

Stamens:

*Number* (*per flower*).—4.

*Filament length.*—2 mm.

*Anthers.*—Shape: Short tube. Length: 4 mm. Color: White.

*Pollen.*—Color: White. Amount: Plentiful.

Pistils:

*Length.*—5 mm.

*Style.*—Length: 3 mm. Color: White.

*Ovaries.*—Length: 1.5 mm. Color: Light green.

*Stigma.*—Shape: Pointed. Color: White.

I claim:

1. A new and distinct variety of *Angelonia* plant substantially as shown and described.

* * * * *

UNITED STATES PATENT AND TRADEMARK OFFICE

CERTIFICATE OF CORRECTION

PATENT NO. : PP 16,818 P2
APPLICATION NO. : 11/059197
DATED : July 18, 2006
INVENTOR(S) : Klaus Olbricht It is certified that error appears in the above-identified patent and that said Letters Patent is hereby corrected as shown below:

On Title Page, Column 1, Line 37, "the following" should read -- The following --

Column 4, Line 7, "(approximately 0.13g/100 seeds)" should read
-- (approximately 0.13g/1000 seeds) --

Signed and Sealed this

Twenty-eighth Day of November, 2006

JON W. DUDAS
*Director of the United States Patent and Trademark Office*